United States Patent
Althaus et al.

(10) Patent No.: US 11,262,357 B2
(45) Date of Patent: Mar. 1, 2022

(54) ACTIVATION ASSAY FOR THE DIAGNOSIS OF A HEPARIN-INDUCED THROMBOCYTOPENIA

(71) Applicant: Siemens Healthcare Diagnostics Products GmbH, Marburg (DE)

(72) Inventors: Harald Althaus, Wetter (DE); Gerlinde Christ, Marburg (DE); Herbert Schwarz, Lohra (DE); Michaela Wicke, Fritzlar (DE); Norbert Zander, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 251 days.

(21) Appl. No.: 16/003,760

(22) Filed: Jun. 8, 2018

(65) Prior Publication Data

US 2018/0356416 A1 Dec. 13, 2018

(30) Foreign Application Priority Data

Jun. 9, 2017 (EP) .................................... 17175143

(51) Int. Cl.
  *G01N 33/543* (2006.01)
  *G01N 33/564* (2006.01)
  *G01N 33/86* (2006.01)
  *G01N 33/68* (2006.01)

(52) U.S. Cl.
  CPC ....... *G01N 33/564* (2013.01); *G01N 33/6893* (2013.01); *G01N 33/86* (2013.01); *G01N 2333/522* (2013.01); *G01N 2400/40* (2013.01); *G01N 2800/222* (2013.01); *G01N 2800/226* (2013.01)

(58) Field of Classification Search
  None
  See application file for complete search history.

(56) References Cited

U.S. PATENT DOCUMENTS

| | | | |
|---|---|---|---|
| 3,996,345 A | 12/1976 | Ullman et al. | |
| 5,466,582 A * | 11/1995 | Amiral | G01N 33/94 435/7.9 |
| 5,763,201 A * | 6/1998 | Tomer | G01N 33/56966 435/7.21 |
| 7,392,140 B2 * | 6/2008 | Serena | G16H 50/70 702/19 |
| 2004/0175696 A1 * | 9/2004 | Ullman | G01N 33/531 435/6.12 |
| 2007/0190582 A1 * | 8/2007 | Poncz | G01N 33/5023 435/7.21 |
| 2012/0040373 A1 | 2/2012 | Ubeda | |

FOREIGN PATENT DOCUMENTS

| | | |
|---|---|---|
| CN | 103344771 A | 10/2013 |
| EP | 0 515 194 | 11/1992 |
| WO | WO-95/06877 | 3/1995 |
| WO | 2015065986 A1 | 5/2015 |

OTHER PUBLICATIONS

Schraw et al., The development of a quantitative enzyme-linked immunosorbent assay to detect human platelet factor, Transfusion 717-724, 2005. (Year: 2005).*

Eichler, P. et al. (2002). "The new ID-heparin/PF4 antibody test for rapid detection of heparin-induced antibodies in comparison with functional and antigenic assays". British Journal of Haematology 116: 887-891.

Leo, A. et al. (Sep. 2003). "Laboratory diagnosis of heparin-induced thrombocytopenia and monitoring of alternative anticoagulants". Clinical and Diagnostic Laboratory Immunology 10(5)—Minireview: 731-740.

Newman, D. J. et al. (1992). "Particle enhanced light scattering immunoassay". Annals of Clinical Biochemistry 29: 22-42.

Peula, R. H. et al. (1995). "Covalent coupling of antibodies to aldehyde groups on polymer carriers" Journal of Materials Science 6: 779-785.

Sheridan, D. et al. (Jan. 1986). "A diagnostic test for heparin-induced thrombocytopenia". Blood Journal 67(1): 27-30.

Udenfriend, S. et al. (Dec. 1985) "Scintillation proximity radioimmunoassay utilizing 125I-labeled ligands" Proceedings of the National Academy of Sciences USA Medical Sciences 82: 8672-8676.

Vengal, L. et al. (2011). "Testing for heparin-induced thrombocytopenia" Cleveland Clinic Laboratories: 4 pages.

Warkentin, T. E. et al. (2010). "The use of well-characterized sera for the assessment of new diagnostic enzyme-immunoassays for the diagnosis of heparin-induced thrombocytopenia". Journal of Thrombosis and Haemostasis 8: 216-218.

Lei, Qian et al.:; "Anti-Heparin/Platelet Factor 4 Antibodies and Heparin-induced Thrombocytopenia"; Journal of Experimental Hematology; No. 2; 2008 [Complete English translation not available—English abstract provided].

Fan, Shaojuan et al.:; "Current Application Status of Luminescent Oxygen Channeling Immunoassay(LOCI) Technology"; "Nanotechnology and Precision Engineering"; vol. 12; No. 2; 2014 [Complete English translation not available—English abstract provided].

Chen, Fang: "Detecting tuberculosis antigens in body fluids, cells and tissues using latex agglutination test"; Foreign Medical, Clinical Biochemistry and Examination Fascicale; No. 6; 1991 English translation not available].

Chinese Office Action dated Jan. 5, 2021 for CN Application No. 2018105735479.

* cited by examiner

Primary Examiner — Gary Counts
(74) Attorney, Agent, or Firm — BakerHostetler

(57) ABSTRACT

The present invention relates to a functional, easily automatable assay for establishing a heparin-induced thrombocytopenia (HIT). What is measured is the secretion of PF4 (platelet factor 4) from activated thrombocytes.

10 Claims, No Drawings

ACTIVATION ASSAY FOR THE DIAGNOSIS OF A HEPARIN-INDUCED THROMBOCYTOPENIA

CROSS-REFERENCE TO RELATED APPLICATIONS

This application claims priority to European Application No. EP17175143.1, filed Jun. 9, 2017, the disclosure of which is hereby incorporated by reference in its entirety.

DESCRIPTION

The present invention is in the field of in vitro diagnostics and relates to a functional, easily automatable assay for establishing a heparin-induced thrombocytopenia.

Heparin-induced thrombocytopenia (HIT) is a thrombotic disorder which can arise during a heparin therapy and can cause life-threatening thromboembolic complications. Affected patients produce antibodies which bind a complex composed of heparin and platelet factor 4 (PF4), so-called anti-PF4/heparin complex antibodies. In vivo, the antibody-bound PF4/heparin complex binds to the thrombocyte surface and causes an activation of the thrombocytes. This leads to a reduction in the thrombocyte count and to an increased risk of thromboembolisms.

Two assay principles are mainly used for HIT diagnosis. The first assay principle is based on the direct detection of anti-PF4/heparin complex antibodies in a body-fluid sample from a patient. To this end, a sample is contacted with PF4/heparin complex or a complex composed of PF4 and another suitable polyanion (such as, for example, polyvinyl sulfonate), and the binding of any anti-PF4/heparin complex antibodies present in the sample is detected using conventional immunological assay methods (e.g., ELISA). However, a disadvantage is that, although the detection of anti-PF4/heparin complex antibodies is sensitive, it is not sufficiently specific, i.e., the detection of the antibodies is not adequate for a positive HIT diagnosis, whereas a negative result appropriately reliably rules out a HIT. Therefore, confirmation by a functional assay based on a second assay principle is recommended.

The second, functional assay principle is based on the detection of the thrombocyte-activating action of the anti-PF4/heparin complex antibodies. In said assay principle, washed thrombocytes from one or more normal donors are mixed with a plasma or serum sample from a patient and with heparin, and thrombocyte activation is measured on the basis of known activation markers, such as, for example, on the basis of the amount of released serotonin (serotonin-release assay), or on the basis of the visually identifiable aggregation reaction of the thrombocytes (HIPA assay). If a patient sample contains anti-PF4/heparin complex antibodies, it is possible to establish a thrombocyte activation which is increased compared to a normal sample (without such antibodies).

To date, the two stated functional assay principles cannot be carried out in traditional laboratories and cannot be carried out in an automated manner because they require a complex manual procedure and therefore can only be executed by trained personnel. Furthermore, the serotonin-release assay requires the removal of the thrombocytes by a centrifugation step and the use of radioactive material.

It is an object of the present invention to provide a functional method for detecting anti-PF4/heparin complex antibodies in a body-fluid sample, which method avoids the aforementioned disadvantages.

It has been found that, through the quantitative determination of PF4 in a reaction mixture containing the sample under investigation, thrombocytes and heparin (or a functionally equivalent, PF4-binding polysaccharide or polyanion), it is possible to establish whether the sample contains anti-PF4/heparin complex antibodies. In the stated reaction mixture, samples containing anti-PF4/heparin complex antibodies clearly cause a secretion of PF4 in the thrombocytes, meaning that an increased amount of PF4 in the reaction mixture indicates the presence of anti-PF4/heparin complex antibodies and thus the existence of a heparin-induced thrombocytopenia.

The present invention thus provides a method for detecting anti-PF4/heparin complex antibodies in a body-fluid sample. The method comprises the steps:

i. providing a reaction mixture by mixing the sample with a thrombocyte-containing reagent and with a PF4-binding, unbranched polysaccharide or with a PF4-binding polyanion;
ii. incubating the reaction mixture; and then
iii. determining the amount of PF4 in the reaction mixture;
iv. comparing the thus determined amount of PF4 in the reaction mixture with a predetermined reference value for the amount of PF4 in reaction mixtures containing body-fluid samples from donors known to contain no anti-PF4/heparin complex antibodies; and
v. establishing the presence of anti-PF4/heparin complex antibodies in the sample when the amount of PF4 that is determined in the reaction mixture exceeds the reference value.

The body-fluid sample preferably originates from a person. Preferably, the body-fluid sample is one which is substantially thrombocyte-free and is, in particular, plasma or serum.

The thrombocyte-containing reagent required for the provision of the reaction mixture is preferably a suspension of washed and resuspended human thrombocytes. The thrombocytes preferably originate from one or more healthy donors known to contain no anti-PF4/heparin complex antibodies. A suitable thrombocyte-containing reagent is prepared by, for example, centrifuging citrate whole-blood samples, to which hirudin has preferably also been added, in order to obtain platelet-rich plasma. Citrate solution and apyrase is again added to the platelet-rich plasma, centrifugation is again carried out, and the cell-free supernatant is subsequently discarded. The pelleted thrombocytes are lastly gathered in a buffered suspension solution.

The body-fluid sample is further mixed with a PF4-binding, unbranched polysaccharide or with a PF4-binding polyanion. A multiplicity of PF4-binding substances which form with PF4 a complex which is bound by the anti-PF4/heparin complex antibodies to be detected are known. Suitable unbranched polysaccharides are, for example, heparin, unfractionated heparin (UFH), fractionated heparin (LMWH), dextran sulfate and fucoidan. Suitable polyanions are, for example, polyvinyl sulfate, polyvinyl sulfonate, polyvinyl phosphate, polyvinyl phosphonate, polystyrene sulfate and polystyrene sulfonate.

Prior to the determination of the amount of PF4 in the reaction mixture, the reaction mixture is incubated for a period in order to allow complex formation between the PF4-binding, unbranched polysaccharide or polyanion and the PF4 protein present in the sample, binding of the anti-PF4/heparin complex antibodies presumably present in the sample to the complex formed and, lastly, activation of the thrombocytes by the binding of the antibody-bound complex to the thrombocyte surface. A typical incubation time is between 5 and 10 minutes, preferably at +37° C.

After sufficient incubation, steps are carried out in order to determine the amount of PF4 in the reaction mixture. The determination of the amount of PF4 in the reaction mixture can be carried out in different ways. Preference is given to binding assays in which the amount of PF4 in the reaction mixture is determined by contacting at least one PF4 binding partner, such as, for example, an anti-PF4 antibody or heparin or a PF4-binding, unbranched polysaccharide or a PF4-binding polyanion, with the reaction mixture. For example, this can be achieved by contacting the reaction mixture (in full or in part) with a PF4 binding partner associated with a solid phase. Unbound constituents are removed by washing, and the amount of the PF4 protein bound to the solid phase is determined with the aid of a second, labeled PFA binding partner (ELISA technique). Particularly suitable anti-PF4 antibodies are monoclonal or polyclonal antibodies having a specificity for free PF4, i.e., having a specificity for PF4 which is not bound to heparin or a functionally equivalent polysaccharide or polyanion, or monoclonal or polyclonal antibodies which bind both free and complexed PF4 protein.

Particular preference is given to homogeneous immunoassays, with which it is possible to dispense with the removal of unbound constituents and thus with wash steps. To this end, the reaction mixture (in full or in part) is mixed with a first and a second anti-PF4 antibody and with a first and a second component of a signal-forming system. The components of the signal-forming system interact such that a detectable signal is formed when the first and the second component of the signal-forming system are brought into close proximity to one another. In this connection, the first anti-PF4 antibody is in an associated state with the first component of the signal-forming system or is associated therewith during the incubation of the reaction mixture, and the second anti-PF4 antibody is in an associated state with the second component of the signal-forming system or is associated therewith during the incubation of the reaction mixture.

In one embodiment of a homogeneous PF4 immunoassay, the components of the signal-forming system are particulate solid phases, for example latex particles, the agglutination of which is determined by means of turbidimetry or nephelometry. To this end, the first component of the signal-forming system consists of a first particulate solid phase, the nature of which is such that said particulate solid phase is in an associated state or is associable with the first anti-PF4 antibody. The first particulate solid phase can be in a bound state with the first anti-PF4 antibody via a covalent bond or via a binding pair X/Y or can be bound therewith in the reaction mix via a binding pair X/Y. Furthermore, the second component of the signal-forming system consists of a second particulate solid phase, the nature of which is such that said particulate solid phase is in an associated state or is associable with the second anti-PF4 antibody. The second particulate solid phase can be in a bound state with the second anti-PF4 antibody via a covalent bond or via a binding pair A/B or can be bound therewith in the reaction mix via a binding pair A/B. Immunoassays based on the principle of particle-enhanced light scattering have been known since about 1920 (for an overview, see Newman, D. J. et al., Particle enhanced light scattering immunoassay. Ann Clin Biochem 1992; 29: 22-42). Preferably, polystyrene particles having a diameter of 0.1 to 0.5 µm, particularly preferably having a diameter of 0.15 to 0.35 µm, are used. Preferably, polystyrene particles having amine, carboxyl or aldehyde functions are used. Further preferably, shell/core particles are used. The synthesis of the particles and the covalent coupling of ligands is, for example, described in Peula, J. M. et al., Covalent coupling of antibodies to aldehyde groups on polymer carriers. Journal of Materials Science: Materials in Medicine 1995; 6: 779-785.

In another embodiment of a homogeneous PF4 immunoassay, the signal-forming system comprises at least one first and one second component which interact such that a detectable signal is formed when they are brought into close proximity to one another and can interact with one another as a result. An interaction between the components is to be understood to mean in particular an energy transfer, i.e., the direct transfer of energy between the components, for example by light or electron radiation and also via reactive chemical molecules, such as, for example, short-lived singlet oxygen. The energy transfer can take place from one component to another, but a cascade of different substances, across which the energy transfer runs, is also possible. For example, the components can be a pair composed of an energy donor and an energy acceptor, such as, for example, photosensitizer and chemiluminescent agent (EP-A2-0515194, LOCI® technology) or photosensitizer and fluorophore (WO 95/06877) or radioactive iodine <125> and fluorophore (Udenfriend et al. (1985) Proc. Natl. Acad. Sci. 82: 8672-8676) or fluorophore and fluorescence quencher (U.S. Pat. No. 3,996,345). Particularly preferably, the first component of the signal-forming system is a chemiluminescent agent and the second component of the signal-forming system is a photosensitizer or vice versa, and the chemiluminescence in the reaction mixture is measured.

The first component and/or the second component of the signal-forming system that can interact with one another can be in an associated state with a particulate solid phase via covalent means or via a specific interaction or in an embedded state in said particulate solid phase. The term particulate solid phase is to be understood to mean noncellular, suspendable particles, such as, for example, metal sols, silica particles, magnetic particles or, particularly preferably, latex particles. Particles having a dimeter of 0.01-10 µm are preferred, and particles having a diameter of 0.1-1 µm are especially preferred.

The nature of the first component of the signal-forming system, the components of which interact such that a detectable signal is formed when they are brought into close proximity to one another and can interact with one another as a result, is such that said first component is in an associated state or is associable with the first anti-PF4 antibody. The first component of the signal-forming system can be in an associated state or be associable with the first anti-PF4 antibody in a direct manner. Preferably, the first component of the signal-forming system is in an associated state or is associable with the first anti-PF4 antibody in an indirect manner. To this end, the first component of the signal-forming system is in an associated state with a particulate solid phase which, in addition, is in an associated state with the first anti-PF4 antibody via covalent means or via a binding pair X/Y or is associable therewith via a binding pair X/Y.

The nature of the second component of the signal-forming system, the components of which interact such that a detectable signal is formed when they are brought into close proximity to one another and can interact with one another as a result, is such that said second component is in an associated state or is associable with the second anti-PF4 antibody. The second component of the signal-forming system can be in an associated state or be associable with the second anti-PF4 antibody in a direct manner. Preferably, the second component of the signal-forming system is in an associated state or is associable with the second anti-PF4 antibody in an indirect manner. To this end, the second component of the signal-forming system is in an associated state with a particulate solid phase which, in addition, is in an associated state with the ligand via covalent means or via a binding pair A/B or is associable therewith via a binding pair A/B.

The "binding partners X and Y" and the "binding partners A and B" are, in both cases, two different molecules which specifically recognize and bind each other. Examples of specific recognition and binding are antibody-antigen interactions, polynucleotide interactions, etc.

Suitable binding pairs X/Y and A/B are especially antigen/antibody combinations, where the binding partner X or A is an antigenic epitope of the anti-PF4 antibody. The antigenic epitope can be a natural sequence or structural epitope of the antibody. The antigenic epitope can also be a heterologous sequence or structural epitope of a modified anti-PF4 antibody. Examples of heterologous sequence or structural epitopes are FLAG- or HIS- or fluorescein-tags, which are used in particular for the labeling of peptides or proteins. Further suitable binding pairs X/Y and A/B are complementary polynucleotides X and Y and A and B, respectively. Particularly preferred binding pairs X/Y and A/B are FLAG-tag/anti-FLAG-tag antibody, HIS-tag/anti-HIS-tag antibody, fluorescein/anti-fluorescein antibody, biotin/avidin and biotin/streptavidin.

It has been found that, with the described homogeneous immunoassays, it is possible to dispense with a centrifugation step for the removal of the thrombocytes in the reaction mixture. This represents a simplification of the method sequence, allowing an automatic processing of the method in common analyzers. In a preferred embodiment of the method according to the invention, the provided reaction mixture is not subjected to a centrifugation step for the sedimentation or removal of the thrombocytes.

After the amount of PF4 in the reaction mixture has been determined, the thus determined amount of PF4 is compared with a predetermined reference value. A suitable reference value is the amount of PF4 which is determined (or has been determined beforehand) with the same method in reaction mixtures containing body-fluid samples from donors known to contain no anti-PF4/heparin complex antibodies. Usually, in order to determine a reference value in a multiplicity of samples from healthy donors known to have no anti-PF4/heparin complex antibodies, the amount of PF4 is determined and then compared with the amount of PF4 for a multiplicity of samples from donors suffering from HIT and having anti-PF4/heparin complex antibodies. A reference value can, for example, then be a threshold which allows the differentiation of samples with anti-PF4/heparin complex antibodies and those without. If the amount of PF4 that is determined in a reaction mixture exceeds the reference value, this makes it possible to establish the presence of anti-PF4/heparin complex antibodies in the sample. By contrast, if the amount of PF4 that is determined in the reaction mixture falls short of the reference value, this makes it possible to establish the absence of anti-PF4/heparin complex antibodies in the sample.

The present invention further provides a method for diagnosing a heparin-induced thrombocytopenia, wherein a method according to the invention is used to detect the presence of anti-PF4/heparin complex antibodies in a body-fluid sample from a patient.

The present invention additionally further provides an assay kit for carrying out a method according to the invention. The assay kit contains at least the following components:
 a. a first reagent containing thrombocytes;
 b. a second reagent containing a PF4-binding, unbranched polysaccharide or a PF4-binding polyanion; and
 c. one or more reagents for the detection of PF4, with at least one reagent containing an anti-PF4 antibody.

The reagent containing thrombocytes is preferably a suspension of washed and resuspended human thrombocytes. The thrombocytes preferably originate from one or more healthy donors known to contain no anti-PF4/heparin complex antibodies. A suitable thrombocyte-containing reagent is prepared by, for example, centrifuging citrate whole-blood samples, to which hirudin has preferably also been added, in order to obtain platelet-rich plasma. Citrate solution and apyrase is again added to the platelet-rich plasma, centrifugation is again carried out, and the cell-free supernatant is subsequently discarded. The pelleted thrombocytes are lastly gathered in a buffered suspension solution. A suitable thrombocyte-containing reagent contains at least $300 \times 10^9$ thrombocytes per liter.

The second reagent contains either
 a PF4-binding, unbranched polysaccharide, preferably from the group consisting of heparin, unfractionated heparin, fractionated heparin, dextran sulfate and fucoidan; or
 a PF4-binding polyanion, preferably from the group consisting of polyvinyl sulfate, polyvinyl sulfonate, polyvinyl phosphate, polyvinyl phosphonate, polystyrene sulfate and polystyrene sulfonate.

The first and the second reagent are intended for the provision of the reaction mixture with the body-fluid sample.

The assay kit also contains one or more reagents for the detection of PF4, with at least one reagent containing an anti-PF4 antibody. A reagent containing an anti-PF4 antibody can be a solid-phase-associated antibody, for example an antibody bound to latex particles or in the well of a microtitration plate. Depending on the assay format, an assay kit contains additional components for the quantitative detection of anti-PF4-antibody-bound PF4, such as, for example, a reagent containing a second antibody labeled with a detectable label.

A preferred assay kit contains a reagent containing a first anti-PF4 antibody and another reagent containing a second anti-PF4 antibody. The first and/or the second anti-PF4 antibodies can be in an associated state with a solid phase and/or a first and second component, respectively, of a signal-forming system, the components of which interact such that a detectable signal is formed when they are brought into close proximity to one another.

The reagents of an assay kit according to the invention can be provided in liquid or lyophilized form. If some or all reagents of the assay kit are present as lyophilisates, the assay kit can additionally contain the solvents required to dissolve the lyophilisates, such as, for example, distilled water or suitable buffers.

The following examples serve to illustrate the present invention and are not to be understood as restrictive.

EXAMPLES

Example 1

Homogeneous Immunoassay for the Detection of Anti-PF4/Heparin Complex Antibodies The LOCI® technology used here involves bringing a latex particle-coupled chemiluminescent compound (Chemibeads) and a latex particle-coupled photosensitizer (Sensibeads) into close proximity to one another through simultaneous binding to an analyte, with the result that singlet oxygen, which is produced by the photosensitizer, can stimulate the chemiluminescent compound.

2 μL of heat-inactivated (at 56° C., 30 min) human plasma sample were mixed with 7.5 μL of a suspension containing washed human thrombocytes from 6 healthy donors (approximately $300 \times 10^9$ thrombocytes/L) and 10 μL of a buffer solution containing 0.2 IU/mL heparin and incubated at 37° C. After 10 minutes, the following components were added to the reaction mixture:

- 50 μL of a "Chemibead" solution containing, in a buffer solution, latex particles coated with a chemiluminescent compound (2-(4-(N,N,ditetradecyl)-anilino-3-phenyl thioxene) and a first monoclonal anti-PF4 antibody (MAK-23/064) which binds both free and complexed PF4 protein (50 μg/mL);
- 50 μL of an antibody solution containing a second biotinylated monoclonal anti-PF4 antibody (MAK-23/074) which binds both free and complexed PF4 protein (5 μg/mL); and
- 100 μL of a "Sensibead" solution containing, in a buffer solution, latex particles coated with a photosensitizer compound (bis-(trihexyl)-silicon-t-butyl-phthalocyanine) and streptavidin (50 μg/mL).

After about 10 minutes, the chemiluminescent signal was measured [kcounts].

The method according to the invention (also called "PF4 release" hereinafter) was used to measure plasma samples from 10 HIT patients, for whom a HIT had been diagnosed on the basis of clinical criteria (4 T score, in some cases with thrombotic event) and the existence of anti-PF4/heparin complex antibodies had been established using two independent, commercially available immunoassays (HemosIL® AcuStar HIT-Ab(PF4-H), Instrumentation Laboratories, and Asserachrom® HPIA-IgG, Diagnostica Stago).

Furthermore, the method according to the invention was used to measure plasma samples from 7 healthy donors (who do not have clinical HIT criteria and also do not have anti-PF4/heparin complex antibodies) and to measure a normal plasma pool (from about 20 plasmas from healthy donors, "FNP").

As "100% control" for the PF4 release assay, an antibody solution containing a thrombocyte-activating anti-PF4/heparin complex antibody (50 μg/mL) was used instead of a plasma sample in order to ascertain the maximum possible secretion of PF4 with the thrombocyte-containing reagent used. To ascertain the secretion of PF4 in % (PF4 release [%]), the raw values measured in kcounts were converted to a proportion of the raw value of the 100% control.

For the purposes of comparison, the stated samples were also measured using the [14C]-serotonin release assay (also called "SRA" hereinafter), in accordance with Sheridan, D. et al. (1986) A diagnostic test for heparin-induced thrombocytopenia. Blood 67 (1): 27-30, which is considered the gold standard.

The assay results are compiled in Table 1.

TABLE 1

Comparison of the PF4 release assay according to the invention with the SRA assay for HIT diagnosis

| | Sample ID | PF4 release [kcounts] | PF4 release [%] | SRA [%] | Thrombot. event |
|---|---|---|---|---|---|
| HIT patients | HIT-50 | 337.1 | 15 | <20 | No |
| | HIT-38 | 534.4 | 24 | 38 | No |
| | HIT-33 | 757.9 | 34 | 55 | Yes |
| | HIT-6 | 739.8 | 33 | 64 | Yes |
| | HIT-17 | 867.3 | 39 | 69 | Yes |
| | HIT-20 | 1295.4 | 58 | 85 | Yes |
| | HIT-12 | 1373.7 | 62 | 88 | Yes |
| | HIT-34 | 1387.8 | 62 | 93 | Yes |
| | HIT-2 | 1814.4 | 81 | 96 | Yes |
| | HIT-28 | 2201.4 | 99 | 100 | Yes |
| | 100% control | 2232.4 | 100 | N/A | N/A |
| Healthy donors | 8864 | 182.6 | 8 | <10 | No |
| | 8098 | 229.0 | 10 | <10 | No |
| | 8848 | 158.0 | 7 | <10 | No |
| | 8408 | 177.5 | 8 | <10 | No |
| | 8396 | 169.7 | 8 | <10 | No |
| | 8866 | 174.5 | 8 | <10 | No |
| | 8784 | 210.8 | 9 | <10 | No |
| | FNP | 161.7 | 7 | <10 | No |
| | Buffer blank | 162.2 | 7 | N/A | N/A |

It becomes apparent that the results of the method according to the invention correlate very well with the results of the SRA gold-standard assay. In all the reaction mixtures containing HIT patient samples, it is possible to detect a PF4 concentration which is significantly increased compared to healthy donors. As threshold (cut-off) for the differentiation of samples containing anti-PF4/heparin complex antibodies from those containing none, it would be possible to define a PF4 release value of ≥15% or even ≥20% (cut-off of SRA assay: ≥20%). However, for a statistically more precise definition of the cut-off value, a distinctly higher number of sample measurements is required.

EMBODIMENTS

Embodiment 1

A method for detecting anti-PF4/heparin complex antibodies in a body-fluid sample, the method comprising the steps:

i. providing a reaction mixture by mixing the sample with a thrombocyte-containing reagent and with a PF4-binding, unbranched polysaccharide or with a PF4-binding polyanion;

ii. incubating the reaction mixture; and then iii. determining the amount of PF4 in the reaction mixture;

iv. comparing the thus determined amount of PF4 in the reaction mixture with a predetermined reference value for the amount of PF4 in reaction mixtures containing body-fluid samples from donors known to contain no anti-PF4/heparin complex antibodies; and v. establishing the presence of anti-PF4/heparin complex antibodies in the sample when the amount of PF4 that is determined in the reaction mixture exceeds the reference value.

Embodiment 2

The method as in Embodiment 1, wherein the thrombocyte-containing reagent contains human thrombocytes from one or more healthy donors known to contain no anti-PF4/heparin complex antibodies.

Embodiment 3

The method as in either of Embodiments 1 and 2, wherein the amount of PF4 in the reaction mixture is determined by contacting at least one anti-PF4 antibody with the reaction mixture.

Embodiment 4

The method as in Embodiment 3, wherein
a first and a second anti-PF4 antibody and
a first and a second component of a signal-forming system, which interact such that a detectable signal is formed when the first and the second component of the signal-forming system are brought into close proximity to one another,
are mixed with the reaction mixture and wherein the first anti-PF4 antibody is in an associated state with the first component of the signal-forming system or is associated therewith during the incubation of the reaction mixture and wherein the second anti-PF4 antibody is in an associated state with the second component of the signal-forming system or is associated therewith during the incubation of the reaction mixture.

Embodiment 5

The method as in Embodiment 4, wherein the first and second component of the signal-forming system comprise in each case a particulate solid phase, and wherein the agglutination of the particulate solid phases in the reaction mixture is measured.

Embodiment 6

The method as in Embodiment 4, wherein the first component of the signal-forming system is a chemiluminescent agent and the second component of the signal-forming system is a photosensitizer or vice versa and wherein the chemiluminescence in the reaction mixture is measured.

Embodiment 7

The method as in any of Embodiments 4 to 6, in which the provided reaction mixture is not subjected to a centrifugation step for the removal of the thrombocytes.

Embodiment 8

A method for diagnosing a heparin-induced thrombocytopenia, wherein a method as in any of Embodiments 1 to 7 is used to detect the presence of anti-PF4/heparin complex antibodies in a body-fluid sample from a patient.

Embodiment 9

An assay kit for carrying out a method as in any of Embodiments 1 to 8, containing the following components:
a. a first reagent containing thrombocytes;
b. a second reagent containing a PF4-binding, unbranched polysaccharide or a PF4-binding polyanion; and
c. one or more reagents for the detection of PF4, with at least one reagent containing an anti-PF4 antibody.

Embodiment 10

The assay kit as in Embodiment 9, wherein the second reagent contains
- a PF4-binding, unbranched polysaccharide from the group consisting of heparin, unfractionated heparin, fractionated heparin, dextran sulfate and fucoidan; or
- a PF4-binding polyanion from the group consisting of polyvinyl sulfate, polyvinyl sulfonate, polyvinyl phosphate, polyvinyl phosphonate, polystyrene sulfate and polystyrene sulfonate.

What is claimed:

1. A method for detecting anti-platelet factor 4(PF4)/heparin complex antibodies in a body-fluid sample, the method comprising:
   i. providing a reaction mixture by mixing the sample with a thrombocyte-containing reagent and with a PF4-binding, unbranched polysaccharide or with a PF4-binding polyanion;
   ii. incubating the reaction mixture;
   iii. determining an amount of PF4 in the reaction mixture;
   iv. comparing the amount of PF4 in the reaction mixture with a predetermined reference value for the amount of PF4 in reaction mixtures containing body-fluid samples from donors known to contain no anti-PF4/heparin complex antibodies; and
   v. establishing the presence of anti-PF4/heparin complex antibodies in the sample when the amount of PF4 in the reaction mixture exceeds the reference value.

2. The method of claim 1, wherein the thrombocyte-containing reagent contains human thrombocytes from one or more body-fluid samples from healthy donors known to contain no anti-PF4/heparin complex antibodies.

3. The method of claim 1, wherein the amount of PF4 in the reaction mixture is determined by contacting at least one anti-PF4 antibody with the reaction mixture.

4. The method of claim 1, wherein
a first and a second anti-PF4 antibody and
a first and a second component of a signal-forming system, which interact such that a detectable signal is formed when the first and the second component of the signal-forming system are brought into close proximity to one another,
are mixed with the reaction mixture and wherein the first anti-PF4 antibody is in an associated state with the first component of the signal-forming system or is associated therewith during the incubation of the reaction mixture and wherein the second anti-PF4 antibody is in an associated state with the second component of the signal-forming system or is associated therewith during the incubation of the reaction mixture.

5. The method of claim 4, wherein the first and second component of the signal-forming system comprise in each case a particulate solid phase, and wherein the agglutination of the particulate solid phases in the reaction mixture is measured.

6. The method of claim 4, wherein the first component of the signal-forming system is a chemiluminescent agent and the second component of the signal-forming system is a photosensitizer or vice versa and wherein the chemiluminescence in the reaction mixture is measured.

7. The method of claim 4, in which the provided reaction mixture is not subjected to a centrifugation step for the removal of thrombocytes.

8. The method of claim 1, wherein the presence of anti-PF4/heparin complex antibodies in the sample is established when the amount of PF4 in the reaction mixture in step iv exceeds the reference value by about 2-fold or greater.

9. The method of claim 1, wherein the presence of anti-PF4/heparin complex antibodies in the sample is established when the amount of PF4 in the reaction mixture in step iv exceeds the reference value by between about 2-fold and about 10-fold.

10. The method of claim 1, wherein the thrombocyte-containing reagent comprises thrombocytes from healthy donors.

* * * * *